(12) United States Patent
Son

(10) Patent No.: US 10,561,397 B2
(45) Date of Patent: Feb. 18, 2020

(54) ULTRASONIC PROBE INJECTION DEVICE USING RCM

(71) Applicant: SPADE CO., LTD, Daejeon (KR)

(72) Inventor: Moonho Son, Daejeon (KR)

(73) Assignee: SPADE CO., LTD, Daejeon (KR)

(*) Notice: Subject to any disclaimer, the term of this patent is extended or adjusted under 35 U.S.C. 154(b) by 223 days.

(21) Appl. No.: 15/522,358

(22) PCT Filed: Oct. 30, 2015

(86) PCT No.: PCT/KR2015/011539
§ 371 (c)(1),
(2) Date: Apr. 27, 2017

(87) PCT Pub. No.: WO2016/068637
PCT Pub. Date: May 6, 2016

(65) Prior Publication Data
US 2017/0333003 A1    Nov. 23, 2017

(30) Foreign Application Priority Data

Oct. 31, 2014   (KR) .................. 10-2014-0149729
Jul. 8, 2015    (KR) .................. 10-2015-0097456

(51) Int. Cl.
| | |
|---|---|
| A61B 8/00 | (2006.01) |
| A61B 90/11 | (2016.01) |
| A61B 17/34 | (2006.01) |
| A61B 8/08 | (2006.01) |
| A61B 90/00 | (2016.01) |

(52) U.S. Cl.
CPC .............. *A61B 8/4444* (2013.01); *A61B 8/00* (2013.01); *A61B 8/08* (2013.01); *A61B 8/0841* (2013.01);
(Continued)

(58) Field of Classification Search
CPC ... A61B 90/11; A61B 8/4444; A61B 17/3403; A61B 17/320036; A61B 17/320016;
(Continued)

(56) References Cited

U.S. PATENT DOCUMENTS 7,240,400 B2 * 7/2007 Bonham .................. E05D 5/06
                                                       16/238
2002/0133079 A1   9/2002 Sandhu
(Continued)

FOREIGN PATENT DOCUMENTS

| JP | 2005192915 A | 7/2005 |
|---|---|---|
| JP | 2005211089 A | 8/2005 |
| KR | 101409836 B1 | 6/2014 |

OTHER PUBLICATIONS

International Search Report of PCT/KR2015/11539, dated Feb. 29, 2016, English translation.

Primary Examiner — David C Eastwood
Assistant Examiner — Milton Truong
(74) Attorney, Agent, or Firm — STIP Law Group, LLC

(57) ABSTRACT

The present invention relates to an ultrasonic probe injection device using a Remote Center of Motion (RCM), the device enabling the insertion angle and the insertion depth of an injection needle of an injection unit to be easily adjusted using one hand, and the insertion angle and the insertion depth of the injection needle of the injection unit to be automatically fixed after adjustment, thereby having the merit of enhancing efficiency in operation, and even if the insertion angle of the injection needle of the injection unit changes, the insertion point reached when the injection needle of the injection unit is inserted is equally maintained, thereby having the merit of enabling a decrease in error with respect to a lesion area.

6 Claims, 13 Drawing Sheets

(52) U.S. Cl.
CPC .......... *A61B 17/3403* (2013.01); *A61B 90/11* (2016.02); *A61B 2017/3413* (2013.01); *A61B 2090/062* (2016.02); *A61B 2090/067* (2016.02); *A61B 2090/378* (2016.02)

(58) Field of Classification Search
CPC ........ A61B 17/3413; A61B 2017/3405; A61B 2017/3407; A61B 2017/3413; A61M 5/425; A61M 5/46; A61M 2005/1586
USPC .......... 600/431, 437, 461; 604/117; 606/130
See application file for complete search history.

(56) References Cited

U.S. PATENT DOCUMENTS

| | | | | |
|---|---|---|---|---|
| 2005/0267373 | A1* | 12/2005 | Lee ...................... | A61B 8/0833 600/471 |
| 2008/0210337 | A1* | 9/2008 | Sommerville ............ | B27C 5/02 144/135.2 |
| 2010/0010505 | A1* | 1/2010 | Herlihy .................. | A61B 90/11 606/130 |
| 2010/0041990 | A1* | 2/2010 | Schlitt ................ | A61B 17/3403 600/439 |
| 2010/0247513 | A1* | 9/2010 | Agee .............. | A61B 17/320036 424/94.67 |
| 2013/0261553 | A1* | 10/2013 | Sheldon ............... | A61B 8/0841 604/117 |
| 2014/0039314 | A1* | 2/2014 | Stoianovici .......... | A61B 8/0841 600/439 |
| 2014/0343406 | A1* | 11/2014 | Damjanovic ........ | A61B 8/0841 600/424 |

\* cited by examiner

ULTRASONIC PROBE INJECTION DEVICE USING RCM

CROSS-REFERENCE TO RELATED APPLICATIONS

This application is the U.S. National Phase under 35 U.S.C. § 371 of International Application No. PCT/KR2015/011539 filed on Oct. 30, 2015, which in turn claims the benefit of Korean Applications No. 10-2014-0149729, filed on Oct. 31, 2014 and No. 10-2015-0097456, filed on Jul. 8, 2015, the disclosures of which are incorporated by reference into the present application.

TECHNICAL FIELD

The present invention relates to an ultrasonic probe injection device using an Remote Center of Motion (RCM), and more particularly, to an ultrasonic probe injection device capable of simply adjusting an insertion depth and an insertion angle of an injection unit inserted into a lesion site, and identically maintaining a target point which an injection needle reaches, even in a case in which an insertion angle of the injection needle is changed.

BACKGROUND ART

Where it has an extreme muscle workout without a warm-up exercise, the muscles are shocked or damaged, so that many patients of feeling pain have been found.

In order to diagnose a muscle damage or a myoma of the patient, it performs a biopsy of an intracorporeal tissue of the patient using musculoskeletal ultrasonic waves in a department of anesthesiology. A method for diagnosing the lesion area of the patient using the conventional ultrasonic probe is as follows.

In a state that the right-handed examiner holds the ultrasonic probe with his right hand, he checks the lesion area while moving the ultrasonic probe. Thereafter, in a state that the ultrasonic probe positioned on his right hand of the examiner is moved to his left hand, after he holds an injection unit with his right hand, he injects the injection liquid into the lesion area or performs a puncture.

However, in the conventional lesion diagnostic method, since the examiner moves the ultrasonic probe held by his right hand to his left hand, the inspection position of the ultrasonic probe is frequently changed. Accordingly, since the image generated on the basis of the ultrasonic echo is changed, there is a problem in that the examiner should reconfirm the lesion area.

As a conventional technique to solve these problems, Korean Patent registration No. 10-1409836 (Registration Date: Jun. 13, 2014) discloses an injection device integrated with an ultrasonic probe. FIG. 1 is a cross-sectional view illustrating a conventional injection device integrated with an ultrasonic probe.

The injection device integrated with the ultrasonic probe includes a main body (10); a support part (11); an injection unit (12); an angle control unit (13); a front and rear power providing unit (14), an operation unit (15), an ultrasonic probe (16), an angle detection unit (17), and a control unit (18).

The main body (10) of a gun shape includes an accommodation space (10a) for providing the installing space of other elements and supporting the support part (11) formed at an inside thereof and the injection unit (12) moved in the front and rear directions in a state that it is supported on one side of the support part (11). Also, a mode switch (10b) and a driving switch (10c) are installed on one side of the main body (10). Here, the mode switch (10b) may select any one of an angle control mode, an injection unit moving mode, and a piston drive mode and the driving switch (10c) serves to drive the corresponding mode selected by the mode switch (10b). In a state that the angle control mode is selected by the mode switch (10b), if driving switch (10c) is turned on, a rotational force providing means (13a) of the angle control unit (13) is driven. In the meantime, in a state that the injection unit moving mode is selected by the mode switch (10b), if driving switch (10c) is turned on, a cylinder rod (15a) of the operation unit (15) is moved back and forth.

However, in the conventional art, since the supporting force is weak, there is a problem in that the insertion angle can be changed during the insertion of the injection unit. Also, since it can adjust the injection unit only up and down in terms of an angle control, there is a problem in that it is difficult to insert the injection unit into the lesion on the side portion or rear portion thereof.

As a conventional technique to solve these problems, Korean Patent registration No. 10-1508919 (Registration Date: Mar. 31, 2015) discloses an injection device of both hands supporting type with ultrasonic probe. FIG. 2 is a perspective view illustrating an injection device of both hands supporting type with ultrasonic probe according to the conventional art.

The injection device of both hands supporting type with ultrasonic probe includes an ultrasonic probe (20); a probe support (21), a shaft (22), a control body (23), an injection angle controller (24), an elevation controller (25), a rotational position controller (26), and an injection unit fixing device (27).

In conventional art, in a state that the ultrasonic probe (20) and the injection unit (28) are coupled to each other, the needle of the injection unit (28) is precisely inserted into the lesion area. Also, when the needle of the injection unit (28) is inserted therein in a state that it supports the ultrasonic probe (20) and the injection unit (28) with both hands, it can prevent the insertion angle of the injection needle from being changed. Moreover, it can facilitate the insertion of the injection needle of the injection unit (28) in all directions of the lesion area.

However, the insertion angle of the injection needle of the injection unit (28) is controlled by the adjustment of the injection angle controller (24). That is, in order to control the insertion angle of the injection needle, in a state that it is controlled by the injection angle controller (24), the injection angle controller (24) should be fixed through the operation of an angle control screw (26a). Accordingly, there is a problem in that it can cause errors in the insertion angle of the injection needle of the injection unit (28).

Also, in the conventional art, the insertion depth of the injection needle of the injection unit (28) is controlled by the adjustment of the elevation controller (25). That is, in order to control the insertion depth of the injection needle of the injection unit (28), in a state that it holds the ultrasonic probe (20) or the probe support (21) with one hand, an elevation controlling knob (25a) should be rotated. Accordingly, there is a problem in that it should use both hands.

DISCLOSURE

Technical Problem

The present invention has been made in an effort to solve the problems of the conceptual description of the conventional art as described above, and an object of the present invention is to provide an ultrasonic probe injection device using a RCM in that even if the insertion angle of the injection needle of the injection unit changes, the insertion point reached when the injection needle of the injection unit is inserted is equally maintained.

Another object of the present invention is to provide an ultrasonic probe injection device using a RCM capable of enabling the insertion angle and the insertion depth of an injection needle of an injection unit to be easily adjusted.

Further another object of the present invention is to provide an ultrasonic probe injection device using a RCM in that the insertion angle and the insertion depth of the injection needle of the injection unit can be adjusted using one hand, so that the injection needle of the injection unit can be precisely inserted into the lesion area.

Further another object of the present invention is to provide an ultrasonic probe injection device using a RCM in that a adjusting gear is spaced apart from a conveying rail by means of an elastic body provided between the conveying rail and the adjusting gear in a state that the insertion depth of the injection needle of the injection unit is controlled by the conveying rail and the adjusting gear, so that the insertion depth of the injection needle of the injection unit is not changed unless it does not apply any force on the adjusting gear.

Technical Solution

According to one aspect of the present invention so as to accomplish these objects, there is provided to an ultrasonic probe injection device using an RCM including: a housing; an ultrasonic probe which includes a knob, a body connected to the knob, and an emitting unit connected to the body, in which the body is rotatably installed in the housing; a lifting body which is installed at an outer circumference of the housing so as to be slidable upward and downward; a support body which has one end coupled to the lifting body and is formed in an arc shape to have the same central axis in a longitudinal direction; and an injection unit fixing body which is installed on the support body and movable along the support body.

Also, the lifting body is slidable upward and downward toward upper and lower sides of the housing by means of a drive means.

Moreover, the drive means includes: a conveying rail provided between an upper protrusion and a lower protrusion formed at the housing; a cut-out groove formed at one side of the conveying rail corresponding to the conveying rail; and an adjusting gear provided in the cut-out groove so as to face the conveying rail and rotated to allow the lifting body to slide along the conveying rail.

Advantageous Effects

According to the present invention, it enables the insertion angle and the insertion depth of an injection needle of an injection unit to be easily adjusted using one hand and the insertion angle and the insertion depth of the injection needle of the injection unit to be automatically fixed after adjustment, thereby having the merit of enhancing efficiency in operation.

Also, according to the present invention, even if the insertion angle of the injection needle of the injection unit changes, the insertion point reached when the injection needle of the injection unit is inserted is equally maintained, thereby having the merit of enabling a decrease in error with respect to the lesion area.

Moreover, according to the present invention, the lifting body can stably slide by the guide rail provided in the housing, so that the injection needle of the injection unit can be precisely inserted therein.

BRIEF DESCRIPTION OF DRAWINGS

The above and other objects, features and advantages of the present invention will be more apparent from the following detailed description taken in conjunction with the accompanying drawings, in which.

REFERENCE SIGNS LIST

Figure 1:
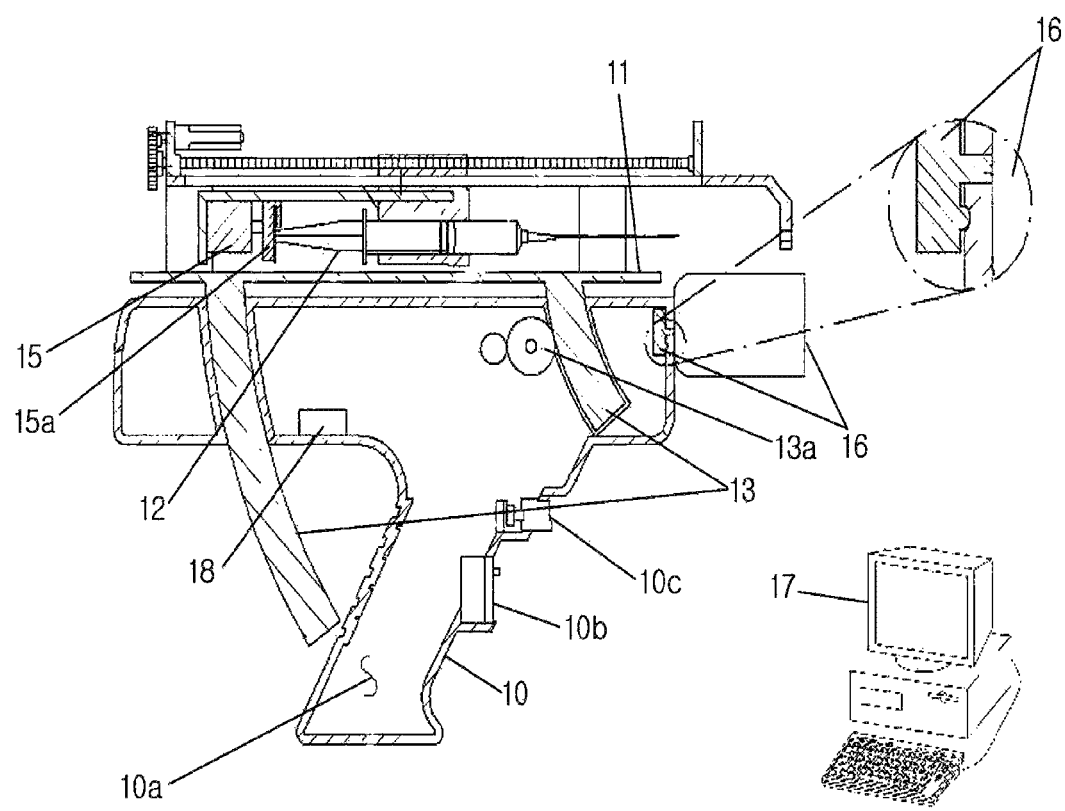
FIG. 1 is a cross-sectional view illustrating a conventional injection device integrated with an ultrasonic probe.
Figure 2:
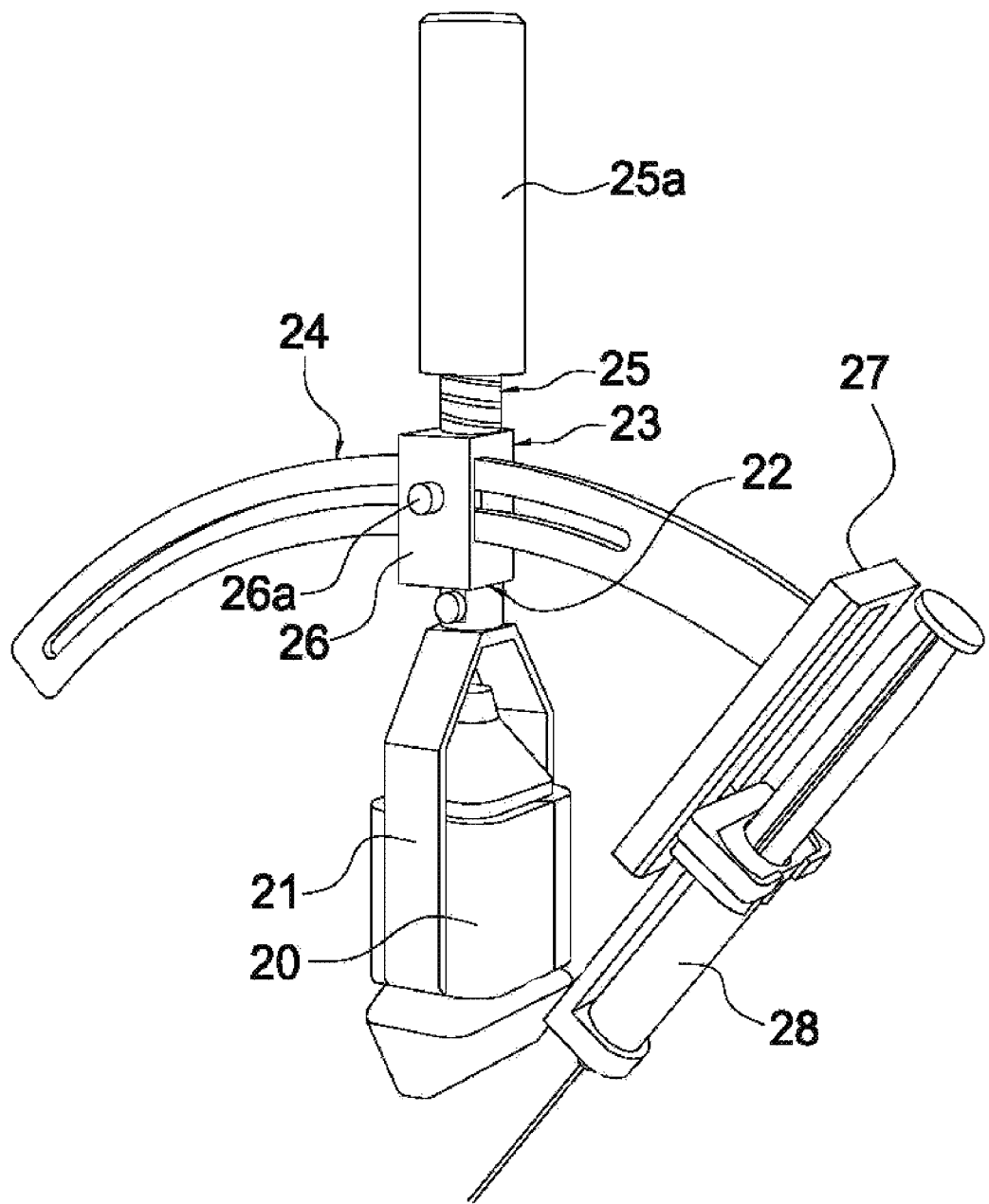
FIG. 2 is a perspective view illustrating an injection device of both hands supporting type with ultrasonic probe according to the conventional art.

100: ultrasonic probe injection device
110: housing
111: upper protrusion
112: lower protrusion
113: guide rail
114: conveying rail
120: ultrasonic probe
121: knob
122: body
123: emitting unit
130: lifting body
131: cut-out groove
132: adjusting gear 133: elastic body
134: number groove
140: support body
141: fixing groove
150: injection unit fixing body
151: fixing member
152: elastic body
153: moving wheel
200: injection unit
210: injection needle
300: control unit

BEST MODE

Mode For Invention

Hereinafter, a preferred embodiment according to the present invention will be described in detail with reference to the accompanying drawings.

The present invention relates to an ultrasonic probe injection device using an RCM capable of facilitating the control of the insertion depth of the injection unit inserted into a lesion section and reducing the procedure time thereof.

Figure 3:
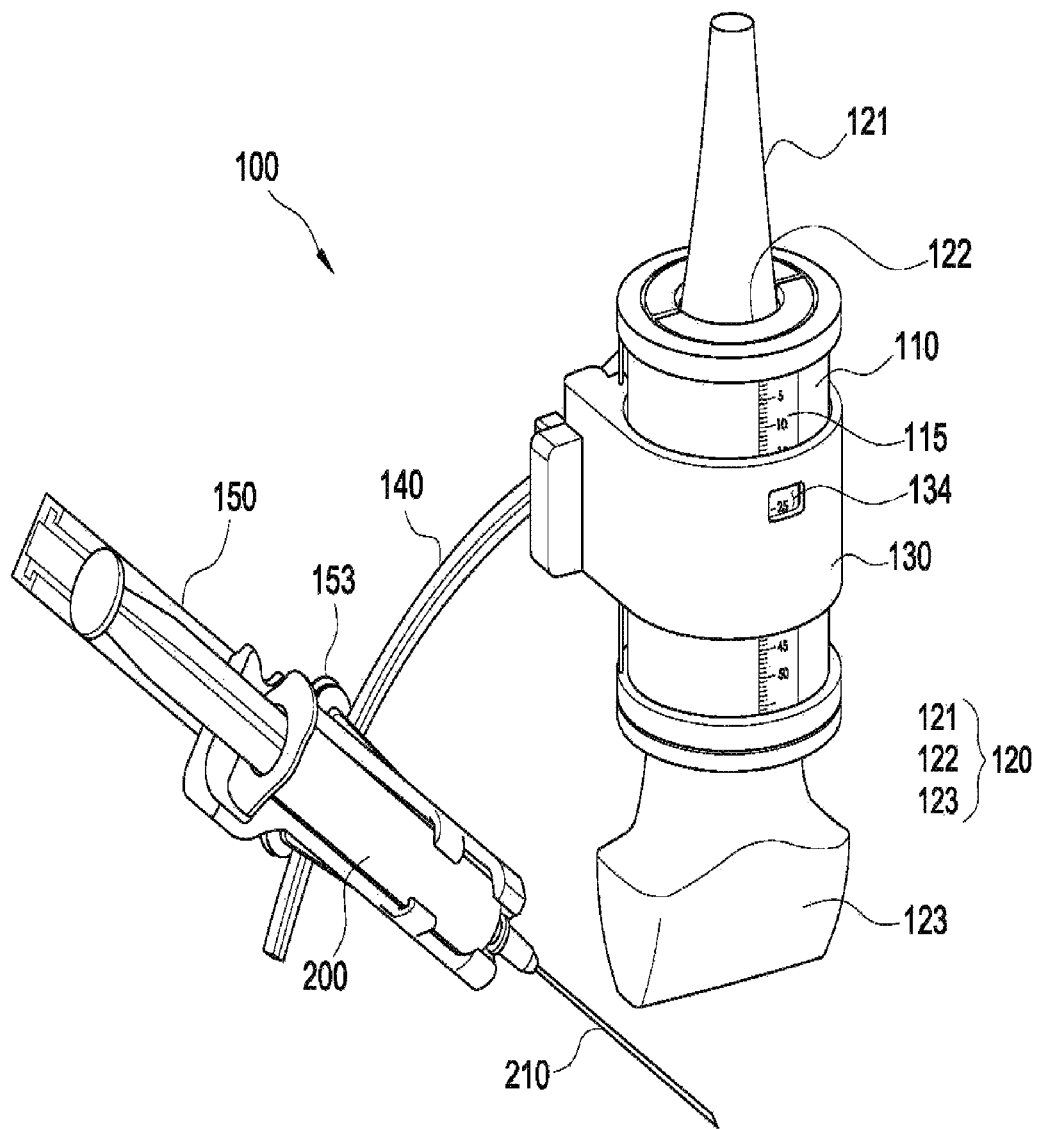
FIG. 3 is a perspective view illustrating a front side of an ultrasonic probe injection device using an RCM according to the present invention.
Figure 4:
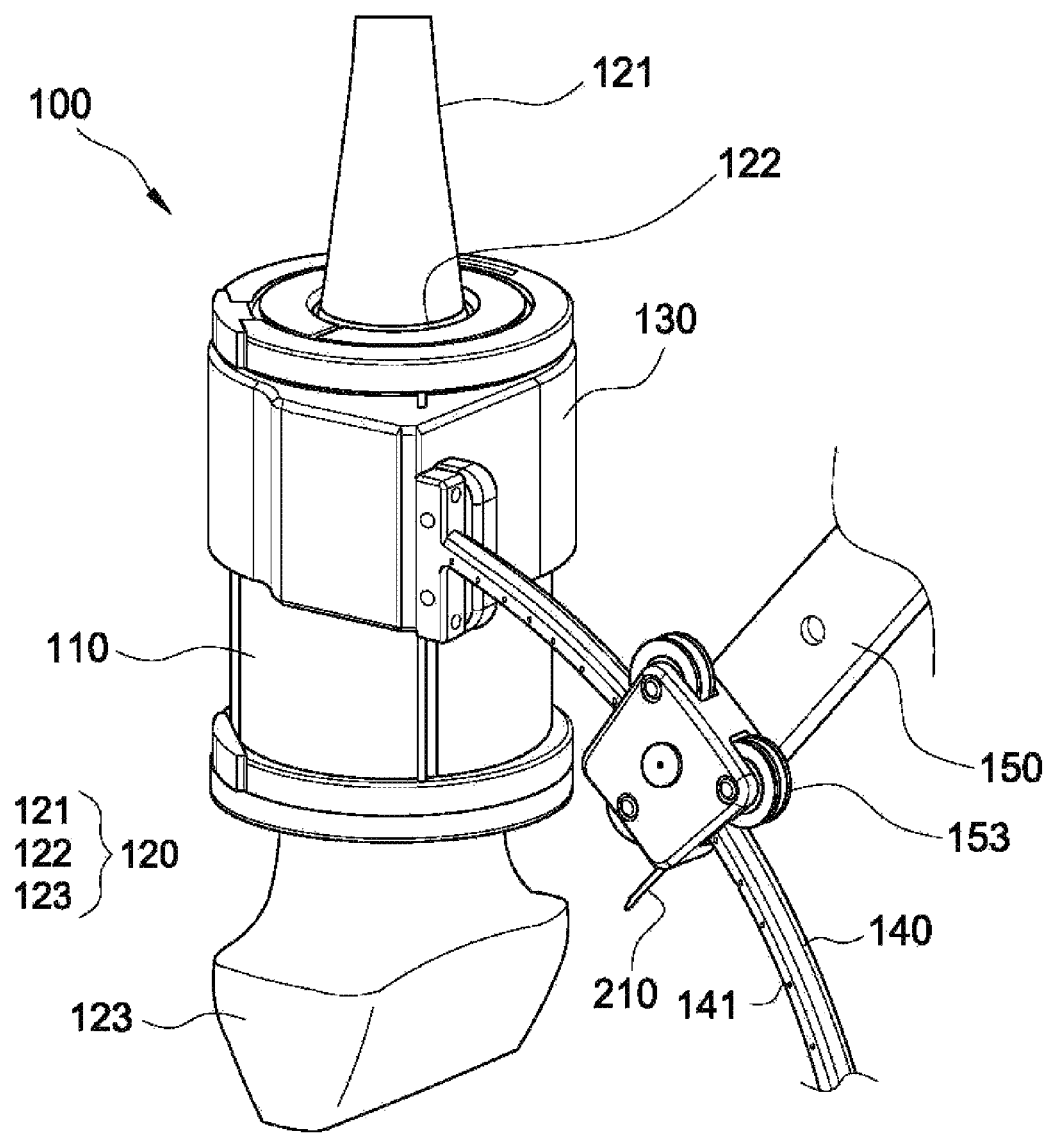
FIG. 4 is a perspective view illustrating a rear side of the ultrasonic probe injection device using the RCM according to the present invention.
Figure 5:
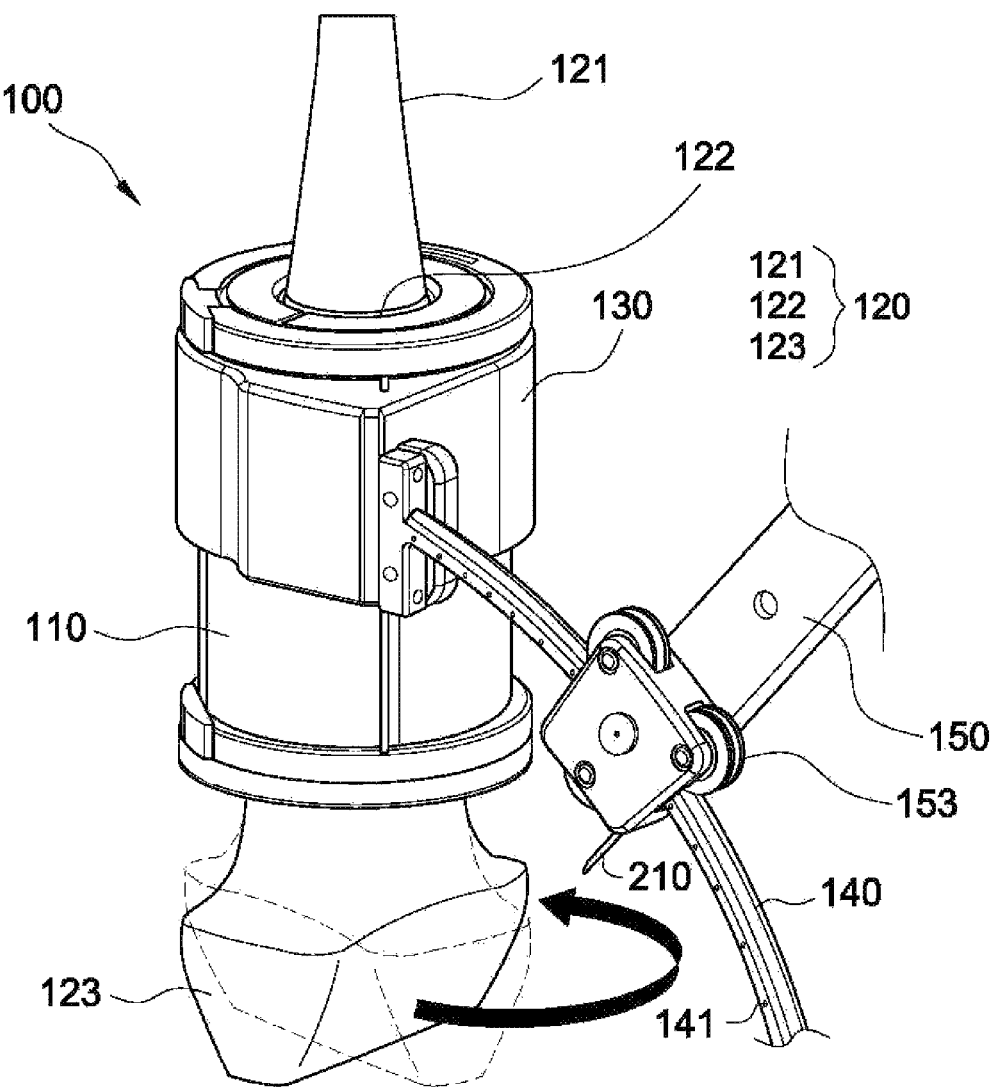
FIG. 5 is a perspective view illustrating a rotation of an ultrasonic probe of the ultrasonic probe injection device using the RCM according to the present invention.
Figure 6:
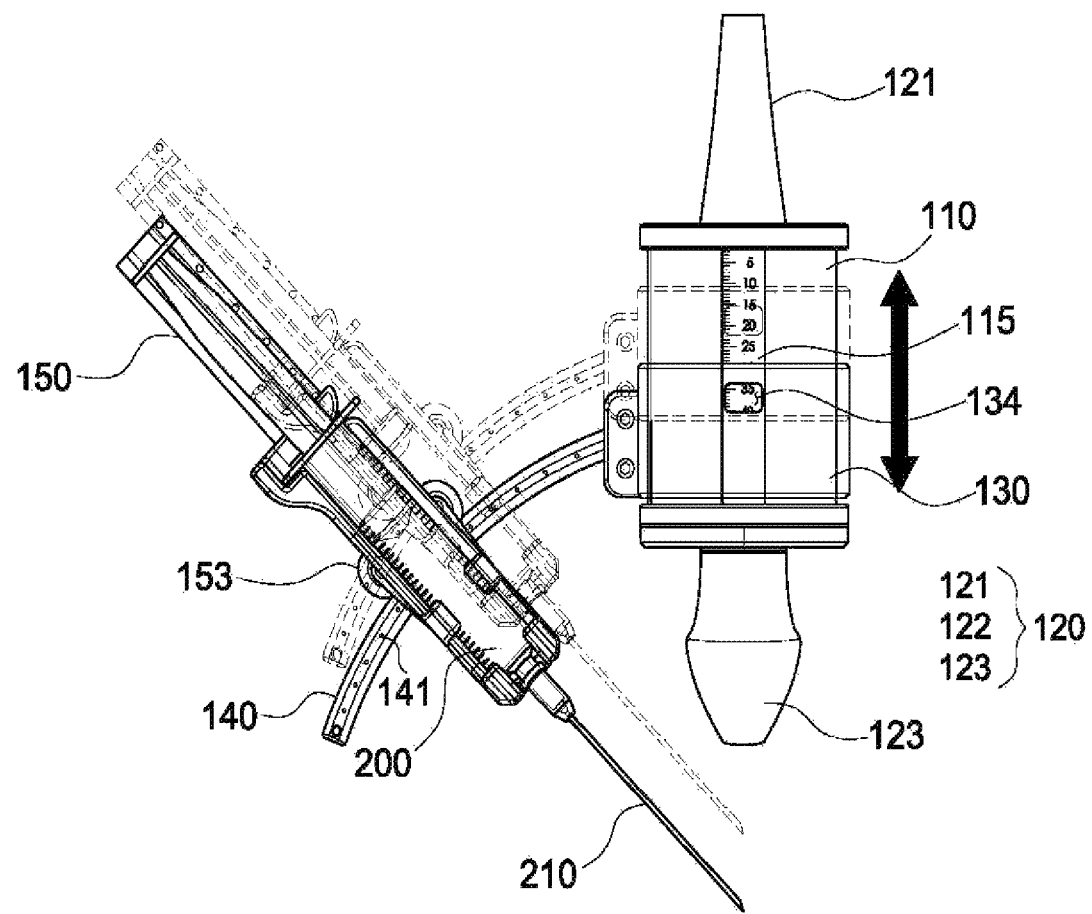
FIG. 6 is a view illustrating a side of a sliding movement of a lifting body of the ultrasonic probe injection device using the RCM according to the present invention.
Figure 7:
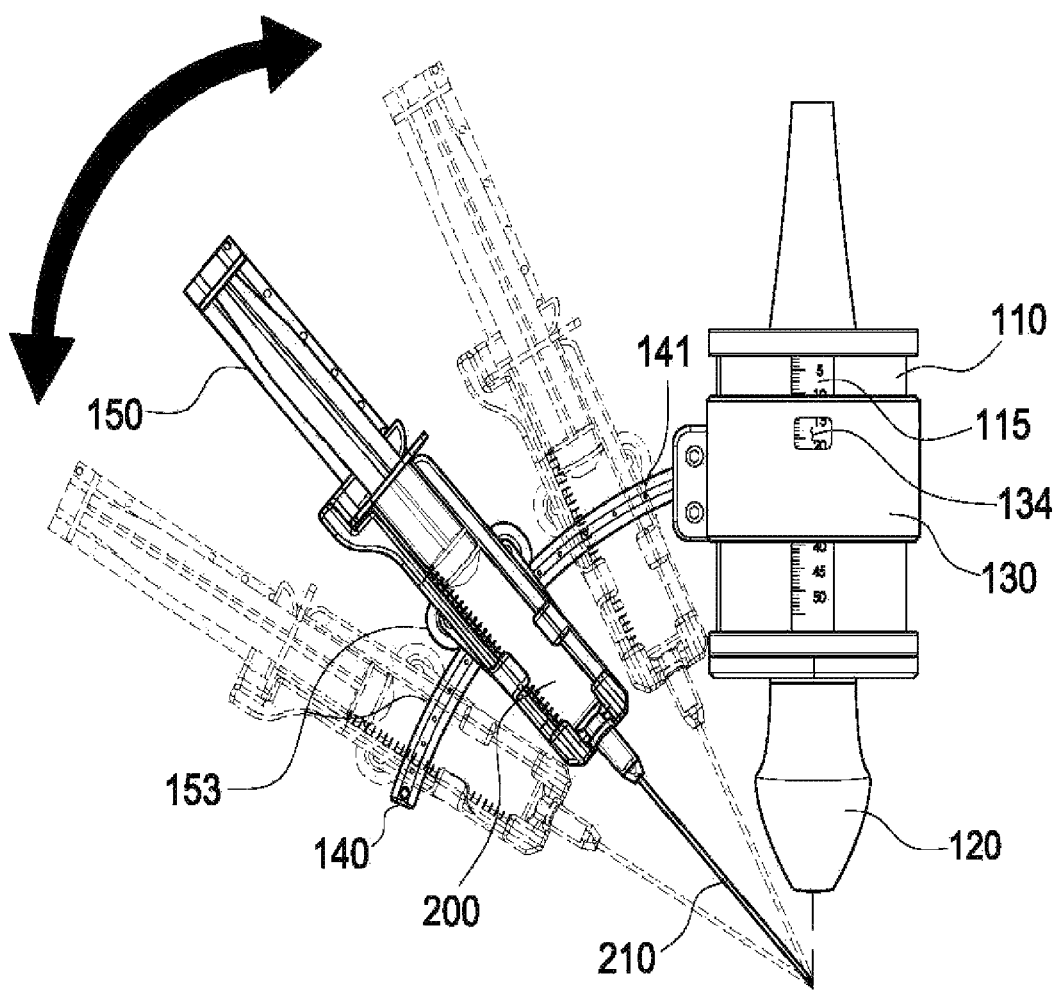
FIG. 7 is a view illustrating a support body and an injection unit fixing body of the ultrasonic probe injection device using the RCM according to the present invention.

FIG. 3 is a perspective view illustrating a front side of an ultrasonic probe injection device using an RCM according to the present invention, FIG. 4 is a perspective view illustrating a rear side of the ultrasonic probe injection device using the RCM according to the present invention, FIG. 5 is a perspective view illustrating a rotation of an ultrasonic probe of the ultrasonic probe injection device using the RCM according to the present invention, FIG. 6 is a view illustrating a side of a sliding movement of a lifting body of the ultrasonic probe injection device using the RCM according to the present invention, and FIG. 7 is a view illustrating a support body and an injection unit fixing body of the ultrasonic probe injection device using the RCM according to the present invention.

Referring to the attached FIGS. 3 and 4, an ultrasonic probe injection device (100) according to the present invention includes a housing (110), an ultrasonic probe (120), a lifting body (130), a support body (140), and an injection unit fixing body (150).

The housing (110) serves to fix and support the ultrasonic probe (120), and is fixedly coupled in a state in which the housing (110) surrounds the ultrasonic probe (120) outside the ultrasonic probe (120). Therefore, a lesion site may be detected in a state in which the ultrasonic probe (120) is stably supported.

Referring to the attached FIG. 5, the ultrasonic probe (120) detects the lesion site based on images created in accordance with ultrasonic echoes, and includes a knob (121), a body (122) connected to the knob (121), and an emitting unit (123) connected to the body (122), and the body (122) is rotatably installed in the housing (110). In this case, the emitting unit (123) of the ultrasonic probe (120) may be rotatably disposed in the body (122).

According to the present invention, the ultrasonic probe (120) transmits an image signal to a monitor device (not illustrated) in a state in which the ultrasonic probe (120) is connected with the monitor device so that the image is displayed, and as a result, the image may be recognized with the naked eye and an internal lesion may be detected.

The technique using the ultrasonic probe (120) and the injection unit (200) is classified in accordance with real time or an approach angle, there are an indirect technique and a real-time technique as the technique which is classified in accordance with real time, and there are an in-plane approach and an out-of-plane approach as the technique which is classified in accordance with the approach angle. In this case, the in-plane approach is a technique in which an injection needle (210) of the injection unit (200) is inserted in parallel with an ultrasonic plane, and an inspector may check a cannula of the injection needle (210) based on the image transmitted through the ultrasonic probe (120), but a procedure technology, which positions the injection needle (210) in parallel with an incident plane of the ultrasonic probe (120), is required. In addition, the out-of-plane approach is a technique in which the injection needle (210) of the injection unit (200) is inserted to be perpendicular to the ultrasonic plane, but the out-of-plane approach has a limitation in that it is difficult to check the cannula of the injection needle (210). Therefore, in most instances, the out-of-plane approach is used only when the in-plane approach is impossible.

The present invention is advantageous in that the in-plane approach and the out-of-plane approach may be carried out together because the body (122) of the ultrasonic probe injection device (100) of the present invention is rotatably installed in the housing (110).

Referring to the attached FIG. 6, the lifting body (130) is installed at an outer circumference of the housing (110) so as to be slidable upward and downward. The upward and downward movement of the lifting body (130) may be carried out by a drive means. The drive means may include guide rails (113), or may include a conveying rail (114), a cut-out groove (131), and an adjusting gear (132). Hereinafter, an exemplary embodiment of the drive means will be described with reference to FIGS. 9 to 11B.

According to the present invention, numbers (115) may be marked at one side of the housing (110), and a number groove (134), which corresponds to the numbers (115) of the housing (110), may be formed at one side of the lifting body (130). The numbers (115) and the number groove (134) serve to indicate an insertion depth of the injection needle (210) of the injection unit (200) according to the sliding movement of the lifting body (130), and with the numbers (115) and the number groove (134), it is possible to easily check the insertion depth of the injection needle (210).

Referring to the attached FIG. 7, the support body (140) has one end coupled to the lifting body (130) and is formed in an arc shape having the same central axis in a longitudinal direction. In addition, the injection unit fixing body (150) is installed on the support body (140) so as to be movable along the support body (140). In more detail, a plurality of moving wheels (153) is installed on the injection unit fixing body (150), and the moving wheels (153) are formed at upper and lower sides of the support body (140) so as to be movable along the support body (140).

According to the present invention, in the ultrasonic probe injection device (100), the injection unit fixing body (150) is moved along the support body (140) by a remote center of motion (RCM) mechanism, and as a result, even in a case in which an insertion angle of the injection needle (210) of the injection unit (200) fixed to the injection unit fixing body (150) is changed, a target point, which the injection needle (210) of the injection unit (200) reaches, may be the same target point before the insertion angle of the injection needle (210) of the injection unit (200) is changed. Therefore, in a state in which the insertion angle and the insertion depth with respect to the lesion site are checked by the ultrasonic probe (120), the injection needle (210) may be inserted while the insertion angle of the injection unit (200) is adjusted so that the injection needle (210) avoids an obstacle at a position where the injection needle (210) is inserted.

That is, even in a case in which the insertion angle of the injection unit (200) is changed to avoid the obstacle, the injection needle (210) reaches the same target point (lesion site).

Figure 8:
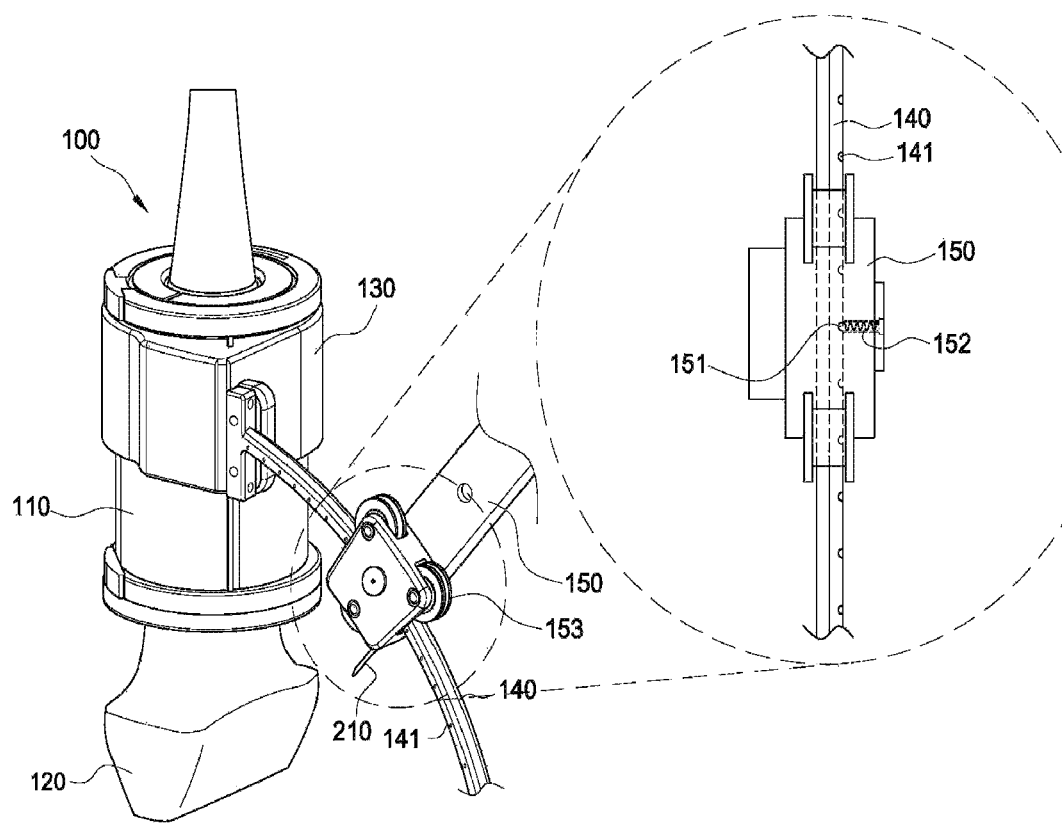
FIG. 8 is a perspective view illustrating a coupling relationship between the support body and the injection unit fixing body of the ultrasonic probe injection device using the RCM according to the present invention.

FIG. 8 is a perspective view illustrating a coupling relationship between the support body and the injection unit fixing body of the ultrasonic probe injection device using the RCM according to the present invention.

Referring to the attached FIG. 8, fixing grooves (141) are formed in a rear surface of the support body (140) so as to be disposed at predetermined intervals in the longitudinal direction, and the injection unit fixing body (150) further has a fixing member (151) which is inserted into the fixing groove (141) to fix the injection unit fixing body (150), and an elastic body (152) which elastically supports the fixing member (151) in a direction in which the fixing member (151) is adjacent to the fixing groove (141).

According to the present invention, in the case of the coupling relationship between the support body (140) and the injection unit fixing body (150), when the injection unit fixing body (150) is completely moved in a state in which the fixing member (151) is elastically supported in a direction toward the fixing groove (141) by the elastic body (152) provided in the injection unit fixing body (150), the fixing member (151) is inserted into the fixing groove (141) by the elastic body (152), and as a result, the injection unit fixing body (150) is fixed to the support body (140).

Therefore, because a separate means for fixing the injection unit fixing body (150) is not required even after the injection unit fixing body (150) is moved, it is possible to adjust an insertion angle of the injection needle (210) of the injection unit (200) by simply moving the injection unit fixing body (150).

Figure 9:
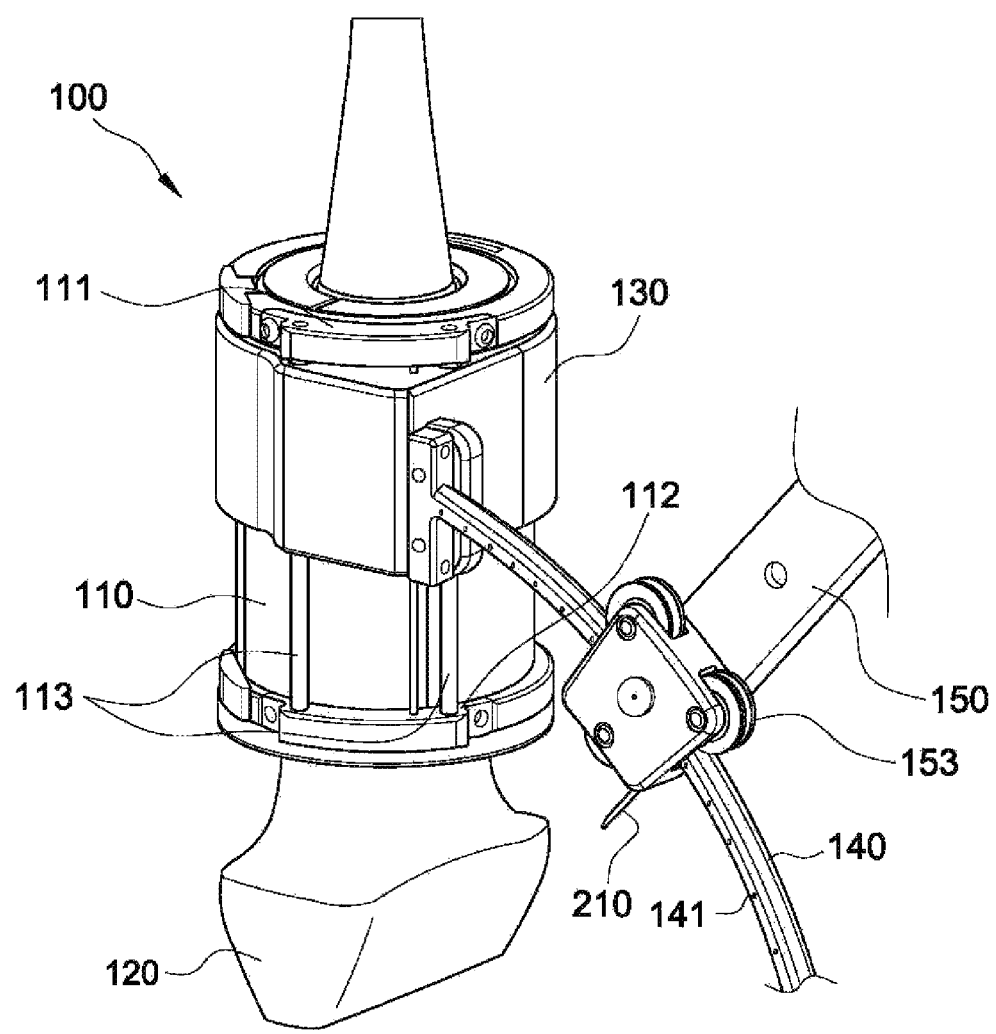
FIG. 9 is a perspective view illustrating the guide rail of the ultrasonic probe injection device using the RCM according to the present invention.

FIG. 9 is a perspective view illustrating the guide rail of the ultrasonic probe injection device using the RCM according to the present invention.

Referring to the attached FIG. 9, the housing (110) has an upper protrusion (111) and a lower protrusion (112), and in this state, the housing (110) further has guide rails (113) which guide the lifting body (130) upward and downward between the upper protrusion (111) and the lower protrusion (112).

At least two guide rails (113) may be provided, and the lifting body (130) may stably slide in a state in which the lifting body (130) is not rotated because of the guide rails (113) even though the lifting body (130) slides toward the upper and lower sides of the housing (110).

Figure 10:
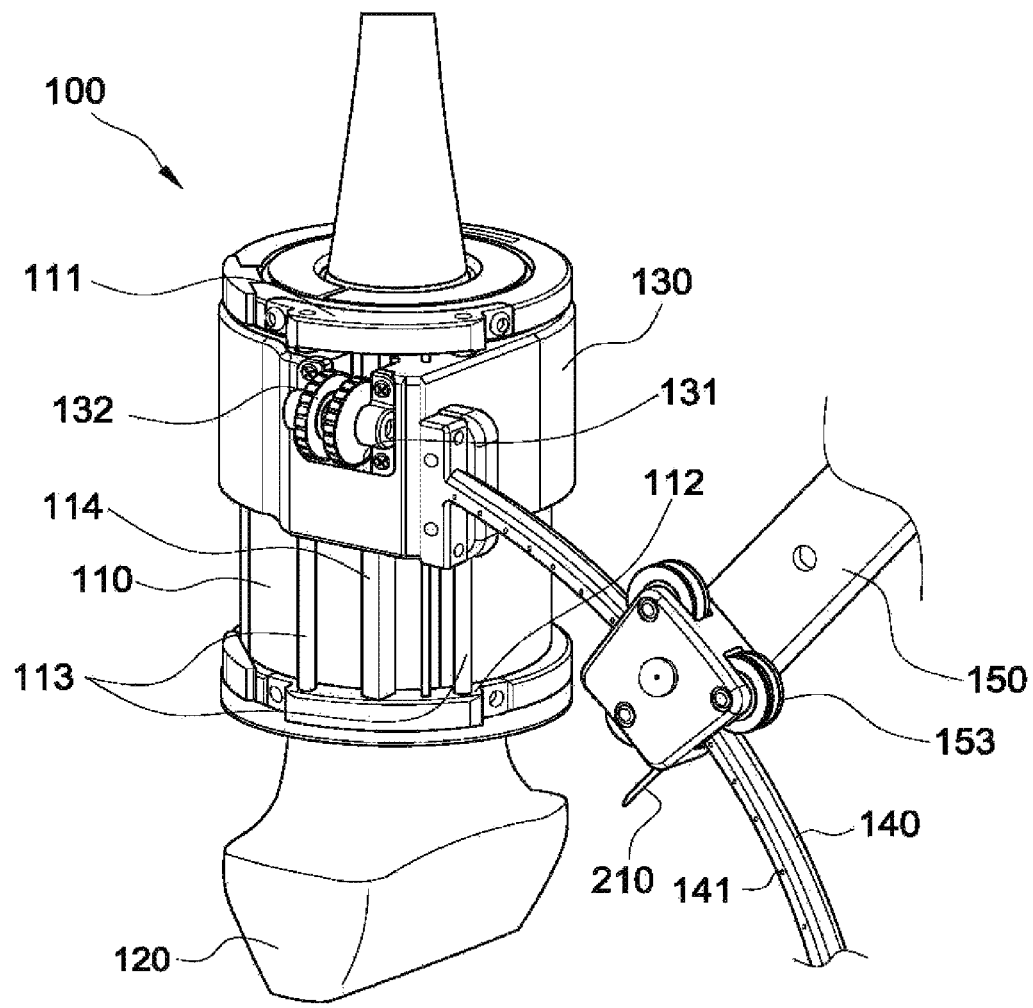
FIG. 10 is a perspective view illustrating the conveying rail, the cut-out groove, and the adjusting gear of the ultrasonic probe injection device using the RCM according to the present invention.
Figure 11A:
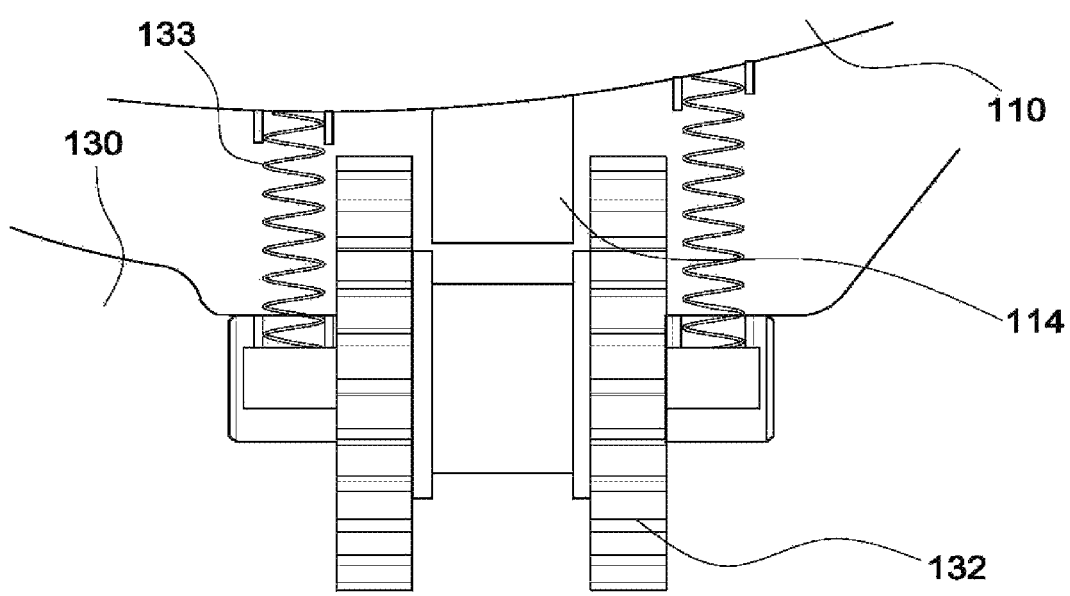
FIGS. 11A and 11B are perspective views illustrating elastic bodies of the ultrasonic probe injection device using the RCM according to the present invention.
Figure 11B:
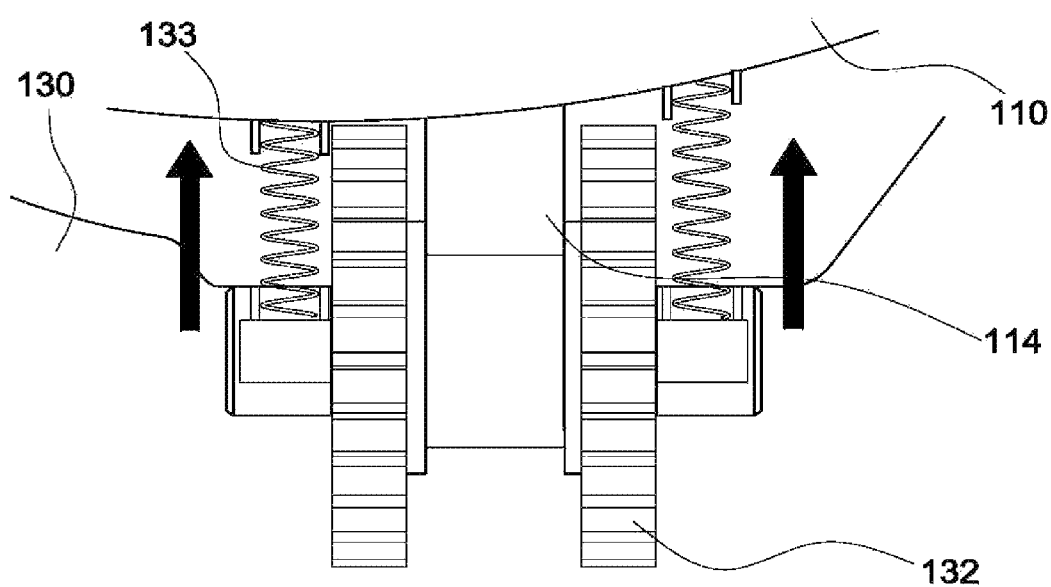

FIG. 10 is a perspective view illustrating the conveying rail, the cut-out groove, and the adjusting gear of the ultrasonic probe injection device using the RCM according to the present invention, and FIGS. 11A and 11B are perspective views illustrating elastic bodies of the ultrasonic probe injection device using the RCM according to the present invention.

Referring to the attached FIG. 10, in a state in which the upper protrusion (111) and the lower protrusion (112) are provided on the housing (110), the conveying rail (114) is further provided between the upper protrusion (111) and the lower protrusion (112), and the lifting body (130) further has the cut-out groove (131) which is formed at a position corresponding to the conveying rail (114), and the adjusting gear (132) which is provided in the cut-out groove (131) so as to face the conveying rail (114) and rotates to allow the lifting body (130) to slide along the conveying rail (114).

The adjusting gear (132) provided in the cut-out groove (131) rotates along the conveying rail (114) so as to enable the lifting body (130) to slide toward the upper and lower sides of the housing (110), and the lifting body (130) may more stably slide by being guided by the guide rail (113).

Referring to FIGS. 11A and 11B, the lifting body (130) further has elastic bodies (133) which are provided between the conveying rail (114) and the adjusting gear (132), and elastically support the adjusting gear (132) in a direction in which the adjusting gear (132) is spaced apart from the conveying rail (114).

In this case, the elastic bodies (133) may have the same configuration as the elastic body (152) provided in the injection unit fixing body (150).

According to the present invention, when force is applied to the adjusting gear (132) in a state in which the elastic bodies (133) of the lifting body (130) elastically support the adjusting gear (132) in the direction in which the adjusting gear (132) is spaced apart from the conveying rail (114), an interval between the conveying rail (114) and the adjusting gear (132) supported by the elastic bodies (133) is decreased, and thus the lifting body (130) may slide toward the upper and lower sides of the housing (110) by the rotation of the adjusting gear (132).

Therefore, if force is not applied to the adjusting gear (132) in a state in which an insertion depth of the injection needle (210) of the injection device (100) is completely adjusted, it is possible to prevent a change in insertion depth of the injection needle (210) of the injection device (100) even in a case in which the adjusting gear (132) is rotated by mistake because the elastic bodies (133) elastically support the adjusting gear (132), and as a result, the injection needle (210) of the injection unit (200) may be precisely inserted with respect to the lesion site.

Figure 12:
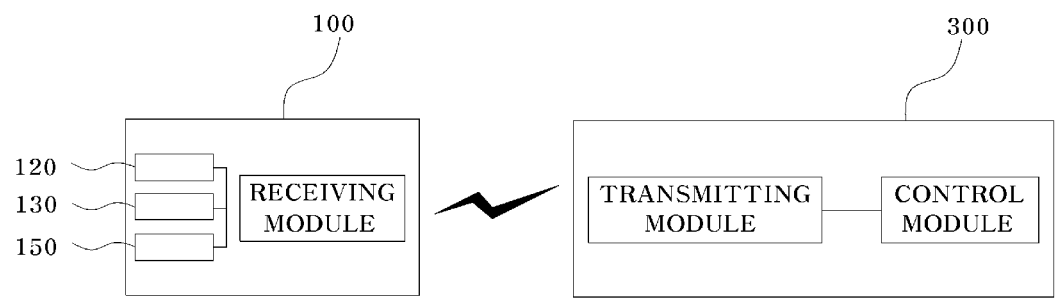
FIG. 12 is a view illustrating remote control of the ultrasonic probe injection device using the RCM according to the present invention.

FIG. 12 is a view illustrating remote control of the ultrasonic probe injection device using the RCM according to the present invention.

According to the present invention, the ultrasonic probe injection device (100) may include a control unit (300) which may remotely control the rotation of the ultrasonic probe (120), the sliding movement of the lifting body (130), and the movement of the injection unit fixing body (150).

Referring to the attached FIG. 12, when a control signal generated in a control module of the control unit (300) is transmitted through a transmitting module of the control unit (300) in a state in which a receiving module is provided in the ultrasonic probe injection device (100) of the present invention, the receiving module may receive the control signal such that the ultrasonic probe (120), the lifting body (130), and the injection unit fixing body (150) may be remotely operated.

Furthermore, the drive means may be configured to be electrically operated.

For example, the drive means may include a combination of a motor which is operated by electrical energy, and gears which are operated by the operation of the motor. In more detail, the rotation of the ultrasonic probe (120), the sliding movement of the lifting body (130), and the movement of the injection unit fixing body (150) may be performed by a combination of a pinion gear which is connected to a shaft of the motor and rotates, and a rack gear which is engaged with the pinion.

According to the present invention, it enables the insertion angle and the insertion depth of an injection needle of an injection unit to be easily adjusted using one hand, and the insertion angle and the insertion depth of the injection needle of the injection unit to be automatically fixed after adjustment, thereby having the merit of enhancing efficiency in operation, and even if the insertion angle of the injection needle of the injection unit changes, the insertion point reached when the injection needle of the injection unit is inserted is equally maintained, thereby having the merit of enabling a decrease in error with respect to a lesion area.

While the present invention has been described with respect to the specific embodiments, it will be apparent to those skilled in the art that various changes and modifications may be made without departing from the spirit and scope of the present invention as defined in the following claims.

INDUSTRIAL APPLICABILITY

The present invention provides the ultrasonic probe injection device using the RCM capable of enabling the insertion point reached when the injection needle of the injection unit is inserted to be is equally maintained, even if the insertion angle of the injection needle of the injection unit changes, so that it is usefully utilized in the field thereof.

The invention claimed is:

1. An ultrasonic probe injection device using an RCM (remote center of motion) comprising:
    a housing (110);
    an ultrasonic probe (120) which includes a knob (121), a body (122) connected to the knob (121), and an emitting unit (123) connected to the body (122), in which the body (122) is rotatably installed in the housing (110);
    a lifting body (130) which is installed at an outer circumference of the housing (110) so as to be slidable upward and downward, wherein the lifting body (130) is slidable upward and downward toward upper and lower sides of the housing (110) by means of a drive means, wherein the drive means comprises: a conveying rail (114) provided between an upper protrusion (111) and a lower protrusion (112) formed at the housing (110); a cut-out groove (131) formed at one side of the conveying rail (114) corresponding to the conveying rail (114); and an adjusting gear (132) provided in the cut-out groove (131) so as to face the conveying rail (114) and rotated to allow the lifting body (130) to slide along the conveying rail (114);
    a support body (140) which has one end coupled to the lifting body (130) and is formed in an arc shape to have the same central axis in a longitudinal direction; and
    an injection unit fixing body (150) which is installed on the support body (140) and movable along the support body (140).

2. The ultrasonic probe injection device as claimed in claim 1, wherein the ultrasonic probe (120) is rotatable inside the housing.

3. The ultrasonic probe injection device as claimed in claim 1, wherein the emitting unit (123) of the ultrasonic probe (120) disposed in the body (122) is rotatable.

4. The ultrasonic probe injection device as claimed in claim 1, further comprising,
    an injection unit (200) comprising an injection needle (210),
    wherein the injection unit (200) is fixed to the injection unit fixing body (150),
    wherein the ultrasonic probe injection device (100) is configured such that a target point, which the injection needle (210) reaches, is unchanged when an insertion angle of the injection needle (210) is changed with respect to the target point during the injection unit fixing body (150) is moved along the support body (140) by the RCM.

5. The ultrasonic probe injection device as claimed in claim 1, further comprising a control unit (300), wherein the control unit remotely controls rotation of the ultrasonic probe (120), a sliding movement of the lifting body (130), and a movement of the injection unit fixing body (150).

6. The ultrasonic probe injection device as claimed in claim 1, further comprising,
    fixing grooves (141) formed in a rear surface of the support body (140), wherein the fixing grooves (141) are disposed at predetermined intervals in the longitudinal direction along the support body (140);
    a fixing member (151) formed in the injection unit fixing body (150), wherein the fixing member (151) is inserted into the fixing groove (141) to fix the injection unit fixing body (150); and
    an elastic body (152), wherein the elastic body elastically supports the fixing member (151) in a direction in which the fixing member (151) is adjacent to the fixing grooves (141).

* * * * *